United States Patent
Villalva et al.

(10) Patent No.: US 10,188,648 B2
(45) Date of Patent: Jan. 29, 2019

(54) SOLID STATE FORMS OF SELEXIPAG

(71) Applicant: TEVA PHARMACEUTICALS INTERNATIONAL GMBH, Jona (CH)

(72) Inventors: Nidia Villalva, Edo de Mexico C.P. (MX); Ivon Cante, Toluca (MX); Martin Aybar, Lerma (MX); Angel Rodriguez, Estado de Mexico (MX); Alejandro Guillen Torres, Estado de Mexico (MX); Hana Kantor, Ostrava (CZ); Ales Gavenda, Ostrava (CZ); Hugo Herrera, Lerma Edo (MX); Alexander Jegorov, Dobra Voda (CZ); Nydia Lopez, San Mateo Atenco (MX)

(73) Assignee: TEVA PHARMACEUTICALS INTERNATIONAL GMBH, Jona (CH)

( * ) Notice: Subject to any disclaimer, the term of this patent is extended or adjusted under 35 U.S.C. 154(b) by 0 days.

(21) Appl. No.: 15/756,719

(22) PCT Filed: Sep. 2, 2016

(86) PCT No.: PCT/US2016/050021
§ 371 (c)(1),
(2) Date: Mar. 1, 2018

(87) PCT Pub. No.: WO2017/040872
PCT Pub. Date: Mar. 9, 2017

(65) Prior Publication Data
US 2018/0214446 A1 Aug. 2, 2018

Related U.S. Application Data

(60) Provisional application No. 62/213,702, filed on Sep. 3, 2015, provisional application No. 62/250,955, filed on Nov. 4, 2015, provisional application No. 62/343,617, filed on May 31, 2016.

(51) Int. Cl.
| | |
|---|---|
| A61K 31/4965 | (2006.01) |
| A61P 9/10 | (2006.01) |
| A61P 9/12 | (2006.01) |
| C07D 241/20 | (2006.01) |

(52) U.S. Cl.
CPC ........... *A61K 31/4965* (2013.01); *A61P 9/10* (2018.01); *A61P 9/12* (2018.01); *C07D 241/20* (2013.01)

(58) Field of Classification Search
CPC ..... C07D 241/20; A61K 31/4965; A61P 9/12; A61P 9/10
See application file for complete search history.

(56) References Cited

U.S. PATENT DOCUMENTS

| | | | |
|---|---|---|---|
| 7,205,302 B2 | 4/2007 | Asaki et al. | |
| 8,791,122 B2 | 7/2014 | Itou | |
| 2014/0148469 A1 | 5/2014 | Itou | |
| 2014/0155414 A1* | 6/2014 | Itou | ............ C07D 241/20 514/255.06 |

OTHER PUBLICATIONS

Caira, M. R., "Crystalline Polymorphism of Organic Compounds." Topics in Current Chemistry, 1998, 198, 163-208.

* cited by examiner

*Primary Examiner* — Alexander R Pagano
*Assistant Examiner* — Ebenezer O Sackey
(74) *Attorney, Agent, or Firm* — Baker & Hostetler LLP

(57) ABSTRACT

The present disclosure relates to solid state forms of Selexipag, in particular selexipag forms IV and V, and processes for preparation thereof, pharmaceutical compositions thereof, and methods of use thereof.

13 Claims, 14 Drawing Sheets

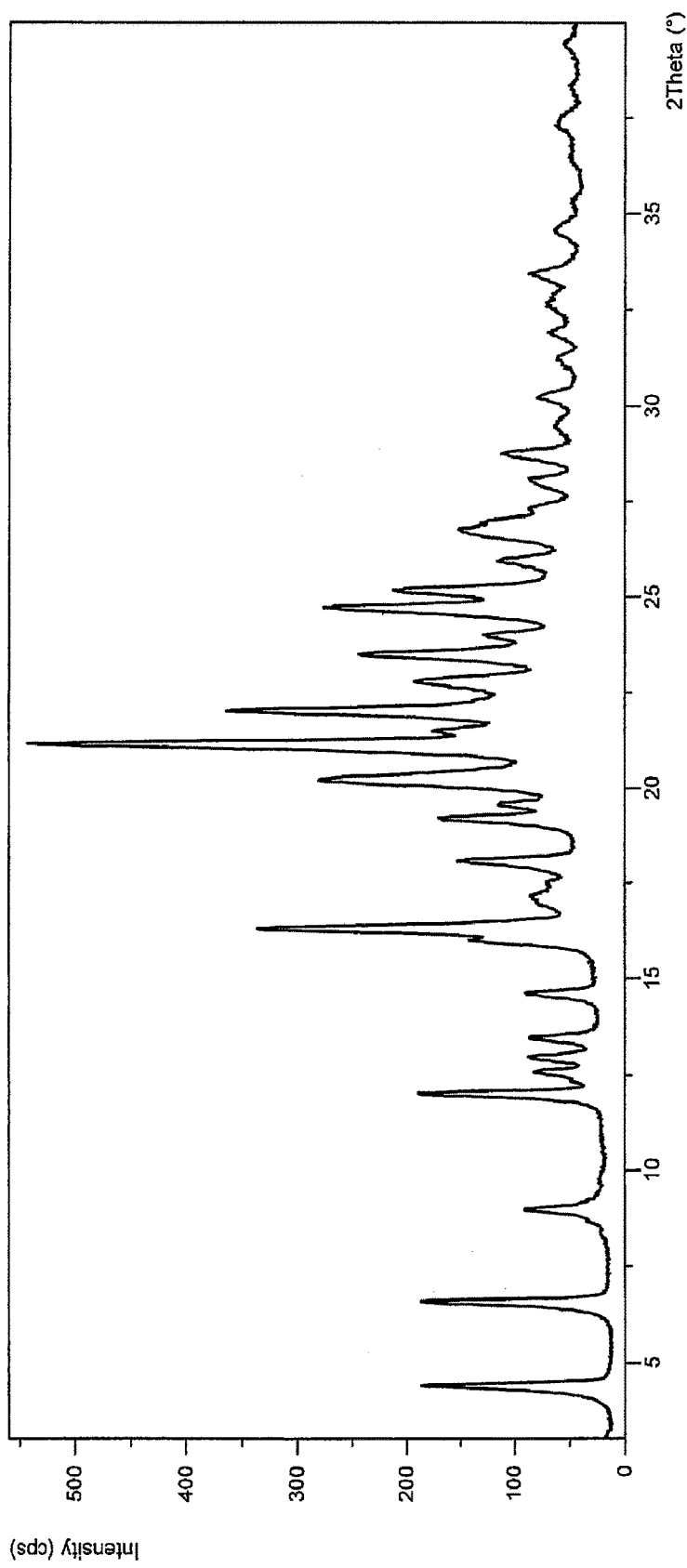
Figure 1: An X-ray powder diffractogram (XRPD) of form IV of Selexipag

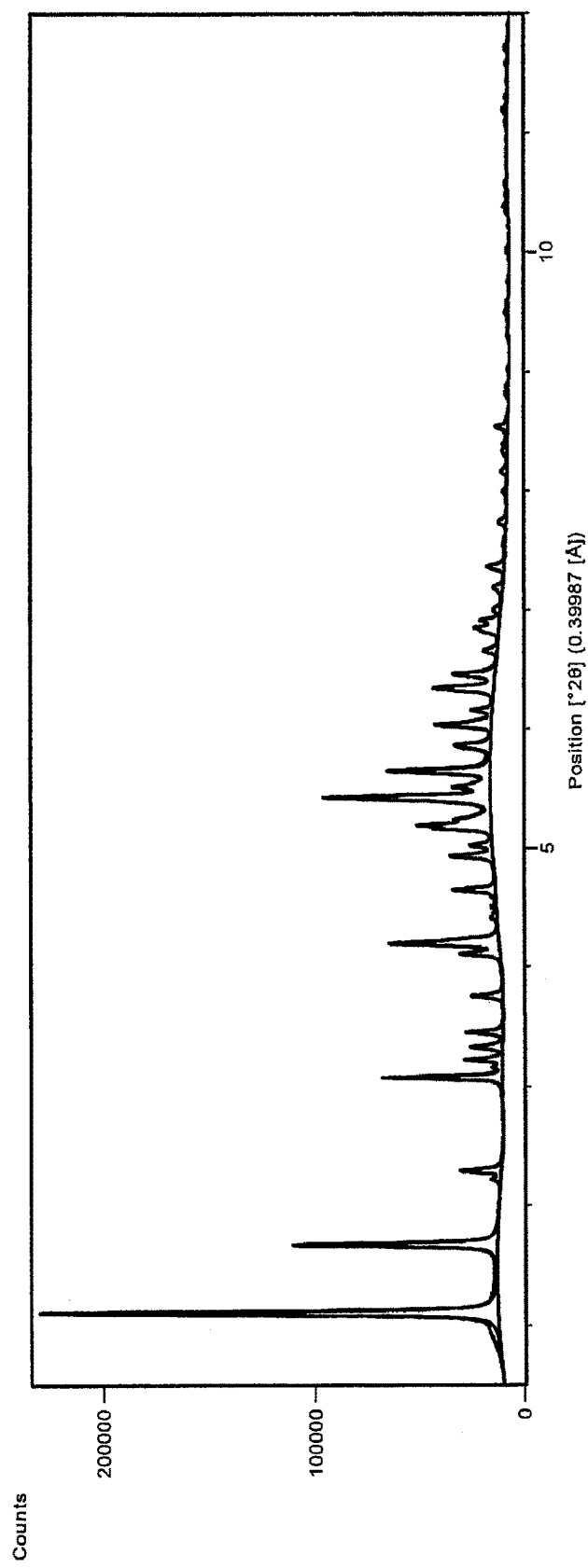

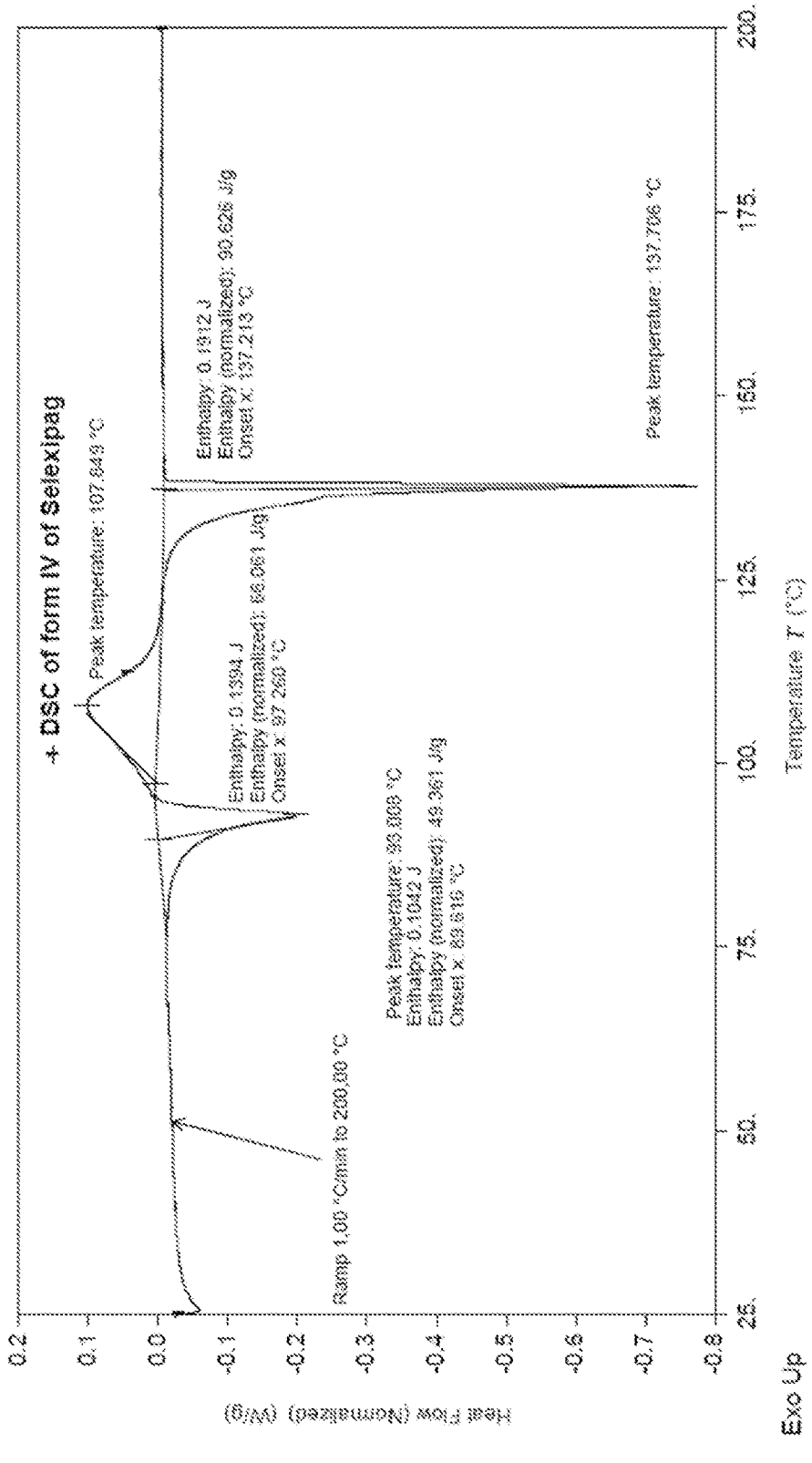

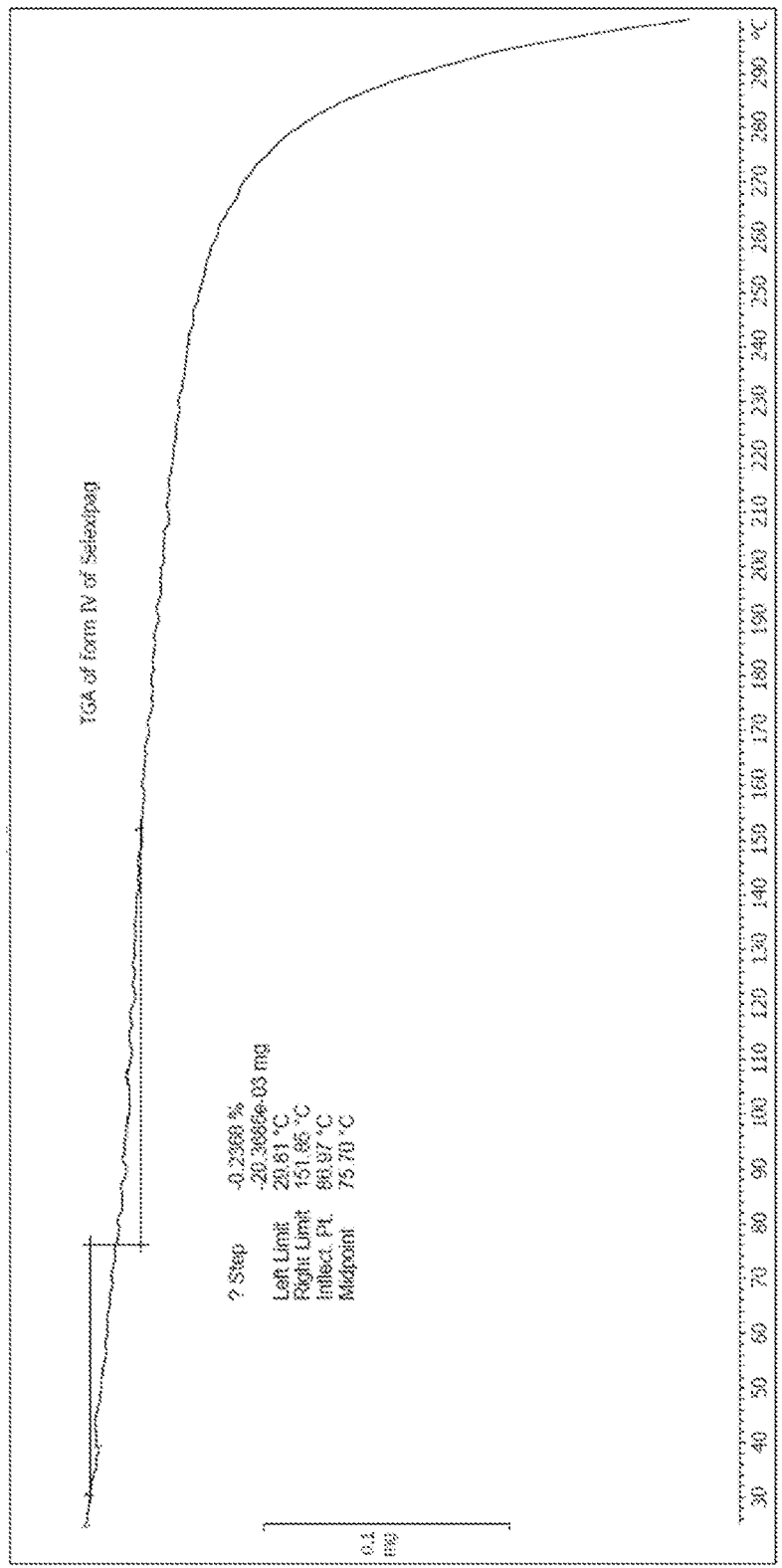
Figure 4: A thermogravimetric analysis thermogram (TGA) of crystalline Selexipag form IV

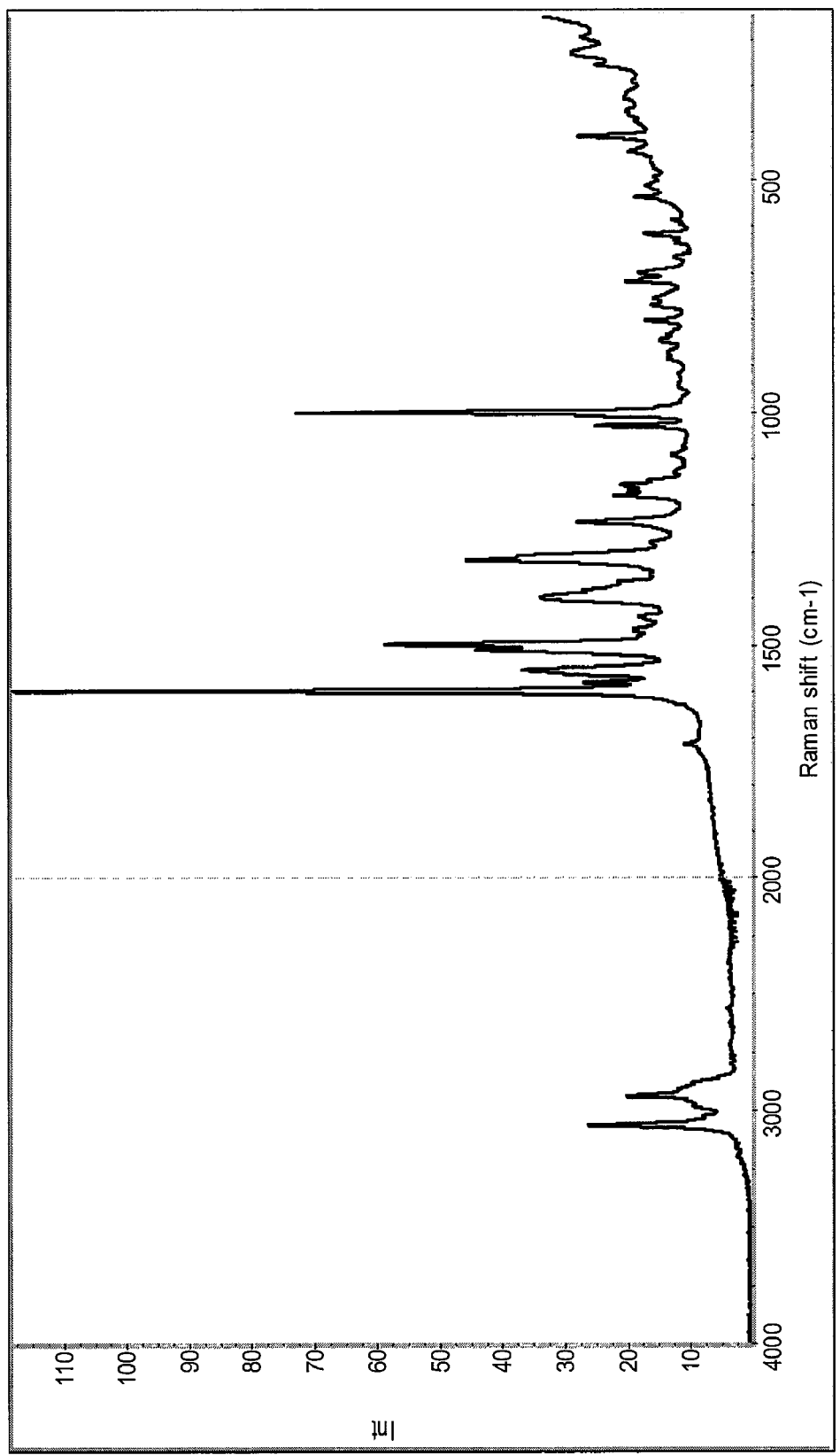
Figure 5: A Raman spectrum of Selexipag form IV (full range)

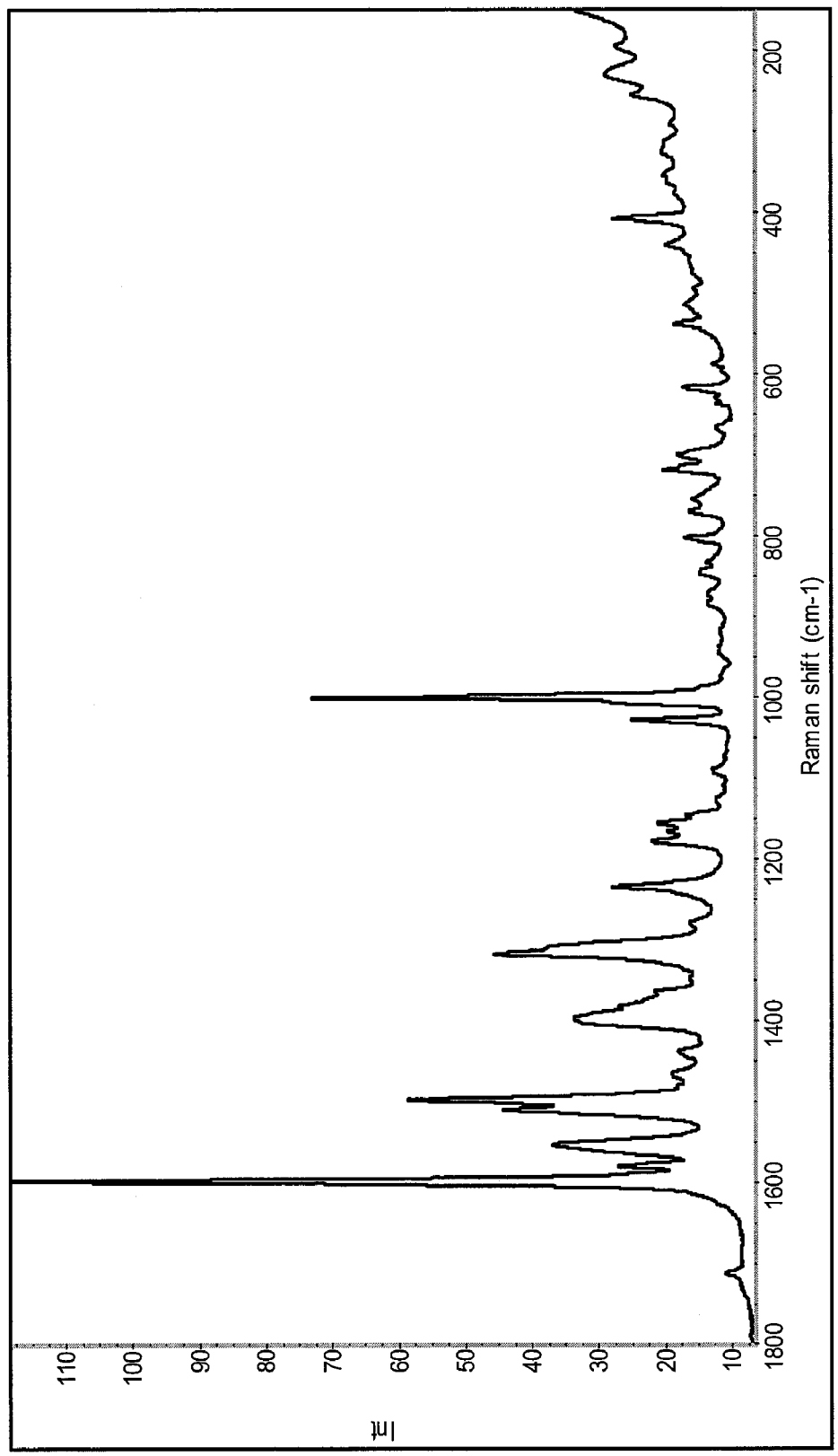
Figure 6: A Raman spectrum of Selexipag form IV – zoom in range from 1800 to 150 cm⁻¹

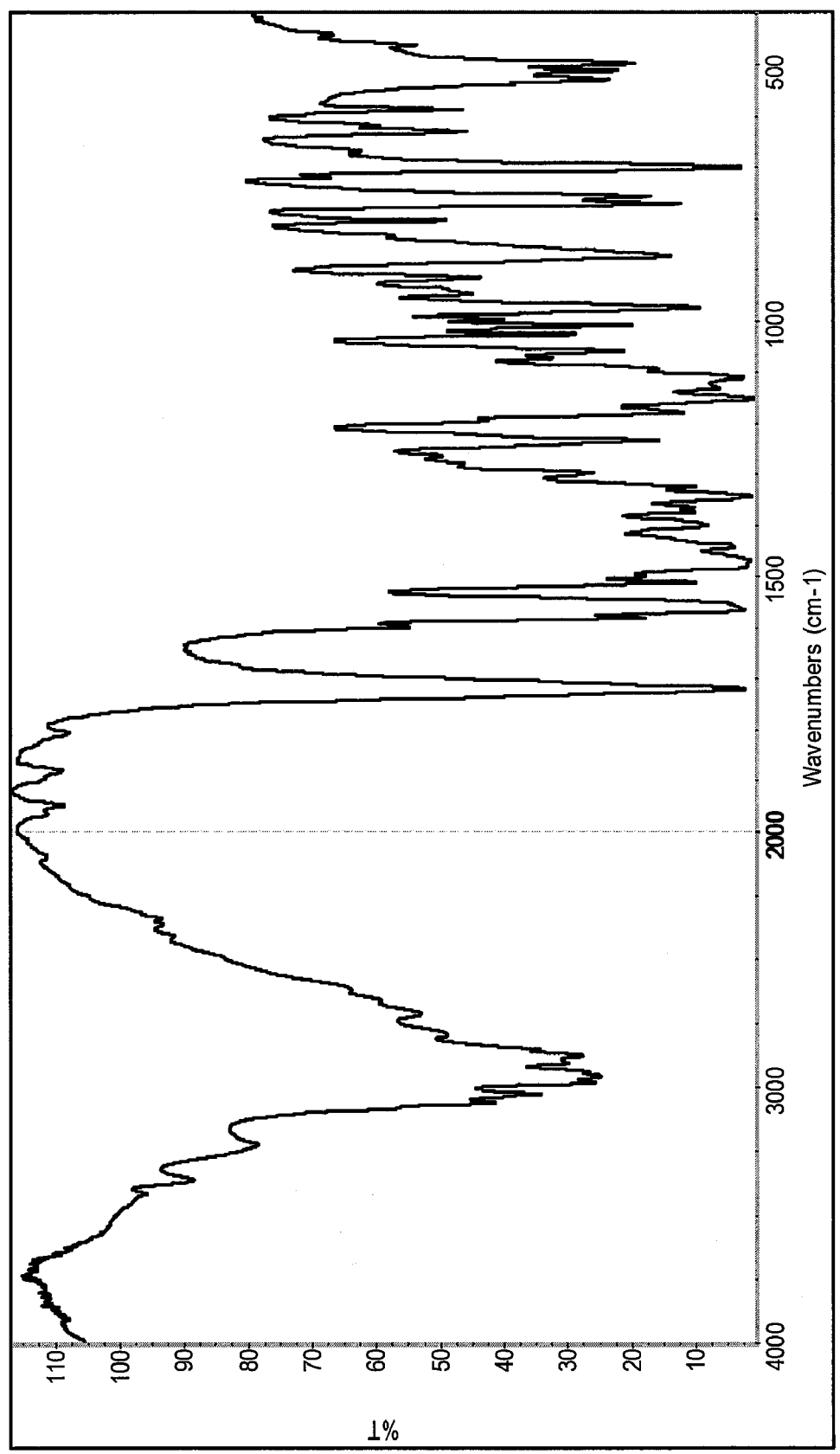
Figure 7: FTIR spectrum of Selexipag form IV – full range

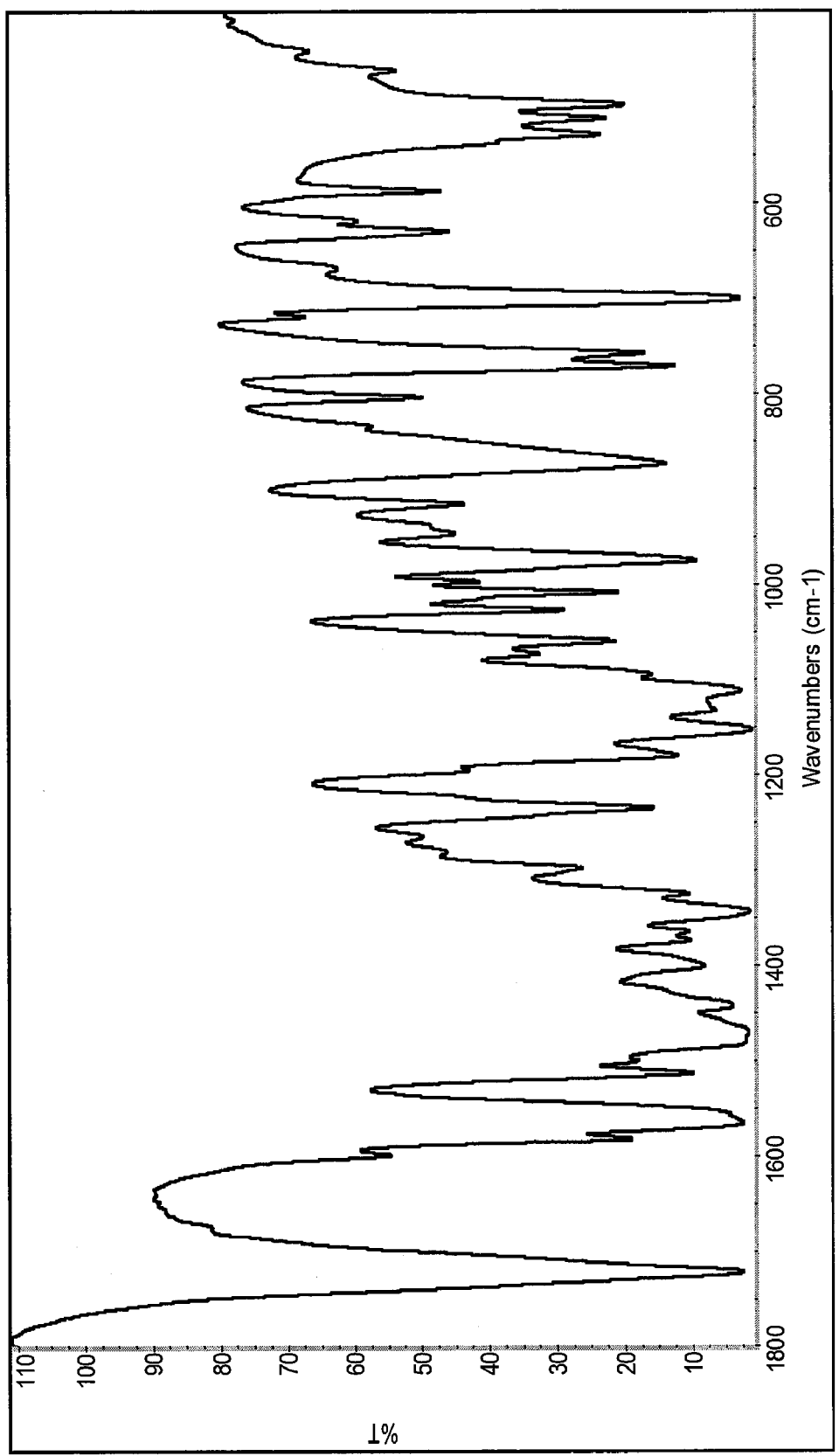
Figure 8: FTIR spectrum of Selexipag form IV – zoom in range from 1800 to 400 cm$^{-1}$

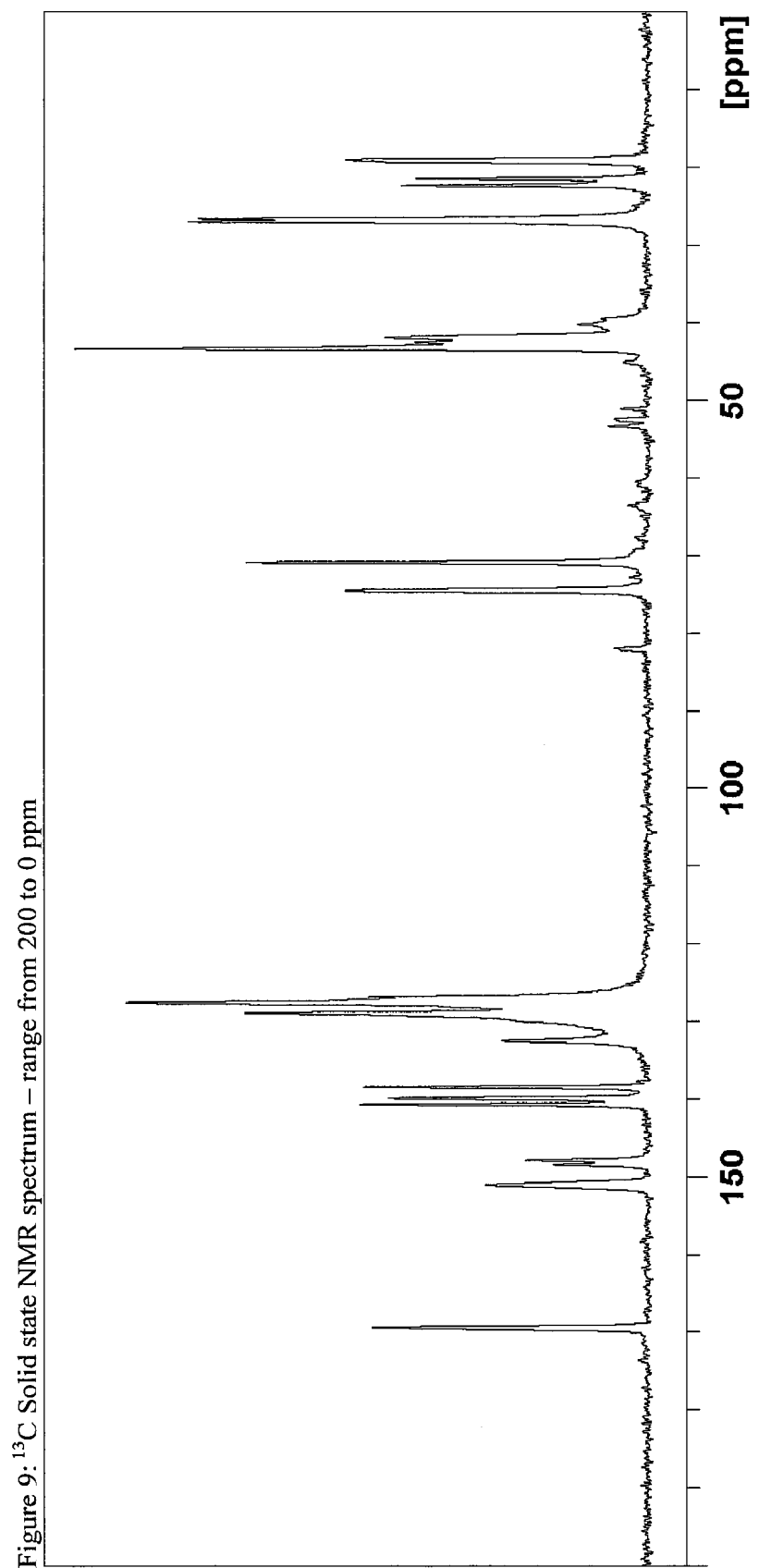
Figure 9: ¹³C Solid state NMR spectrum – range from 200 to 0 ppm

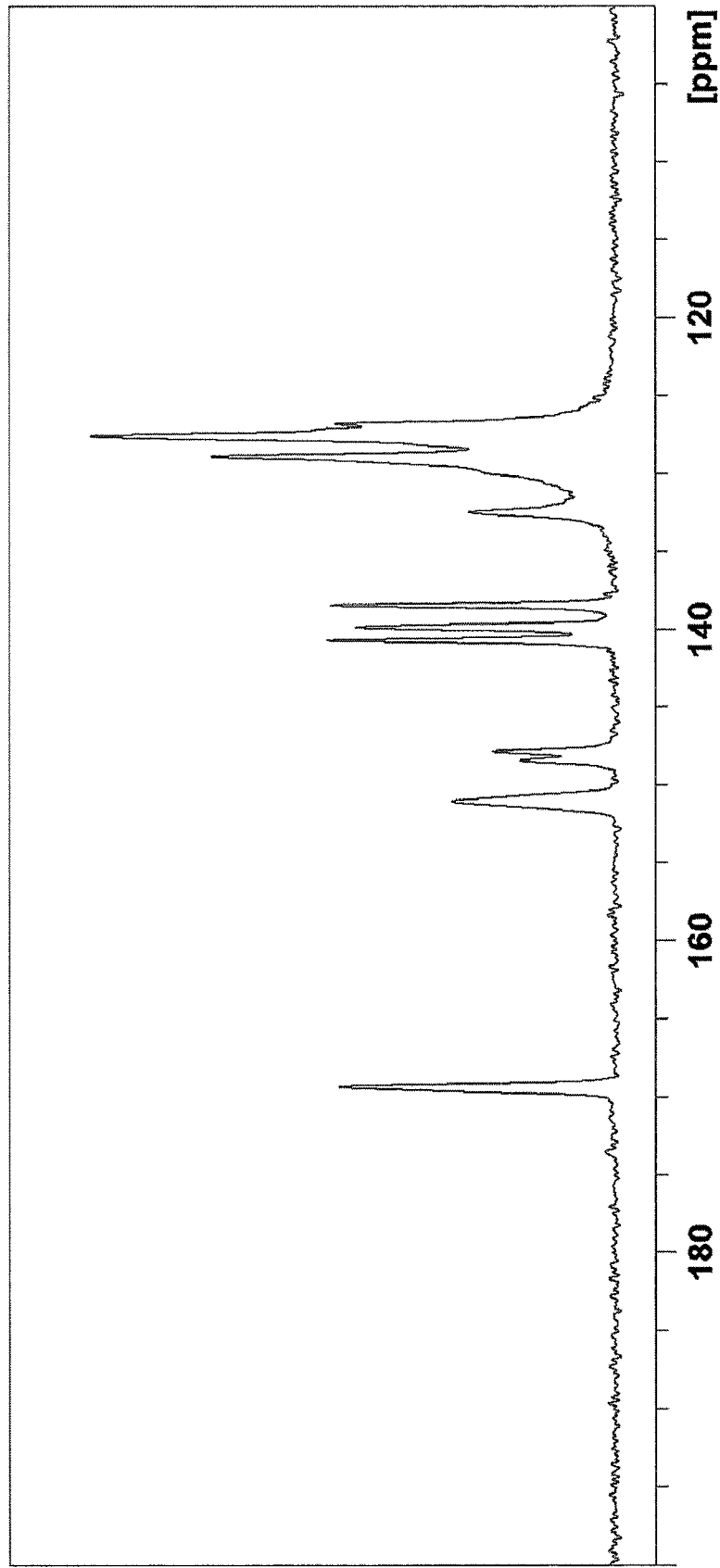

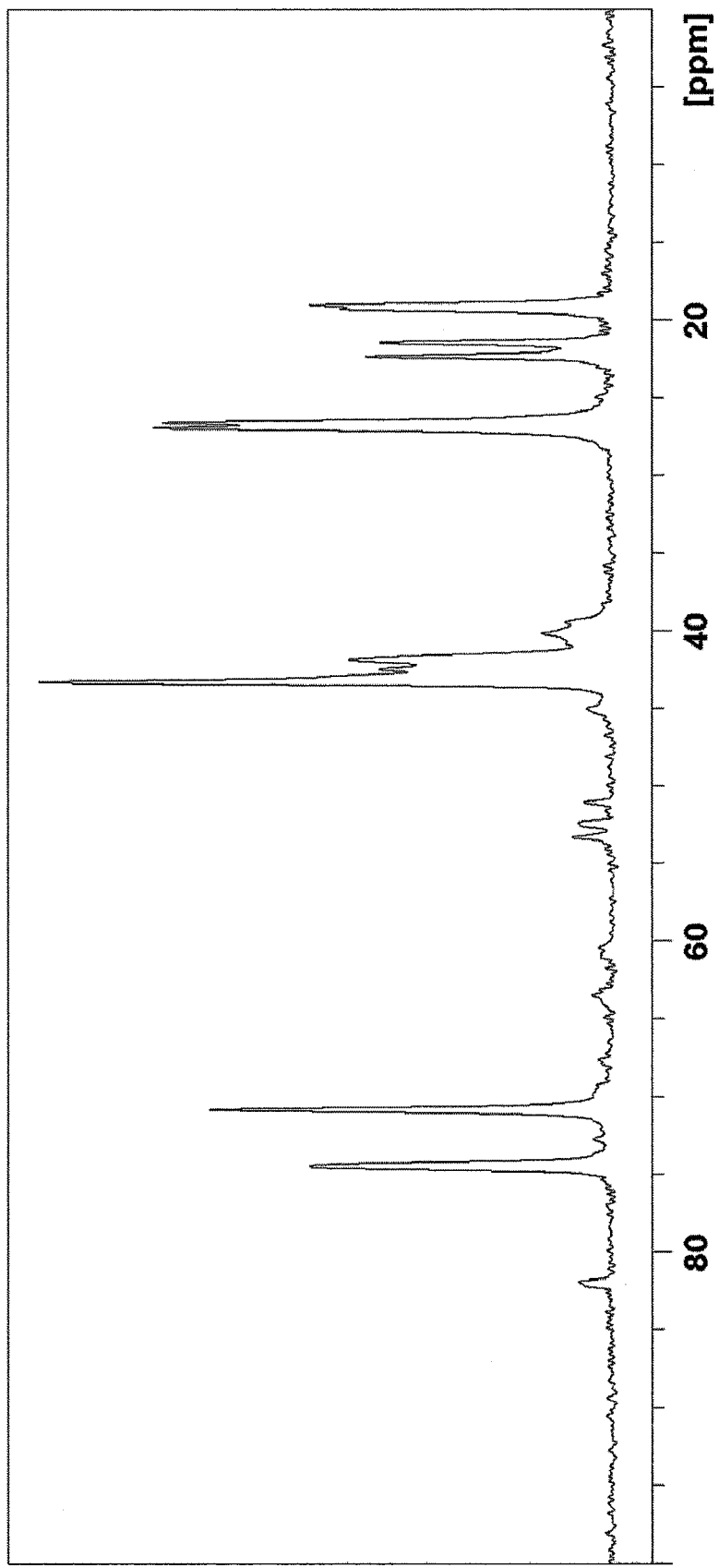

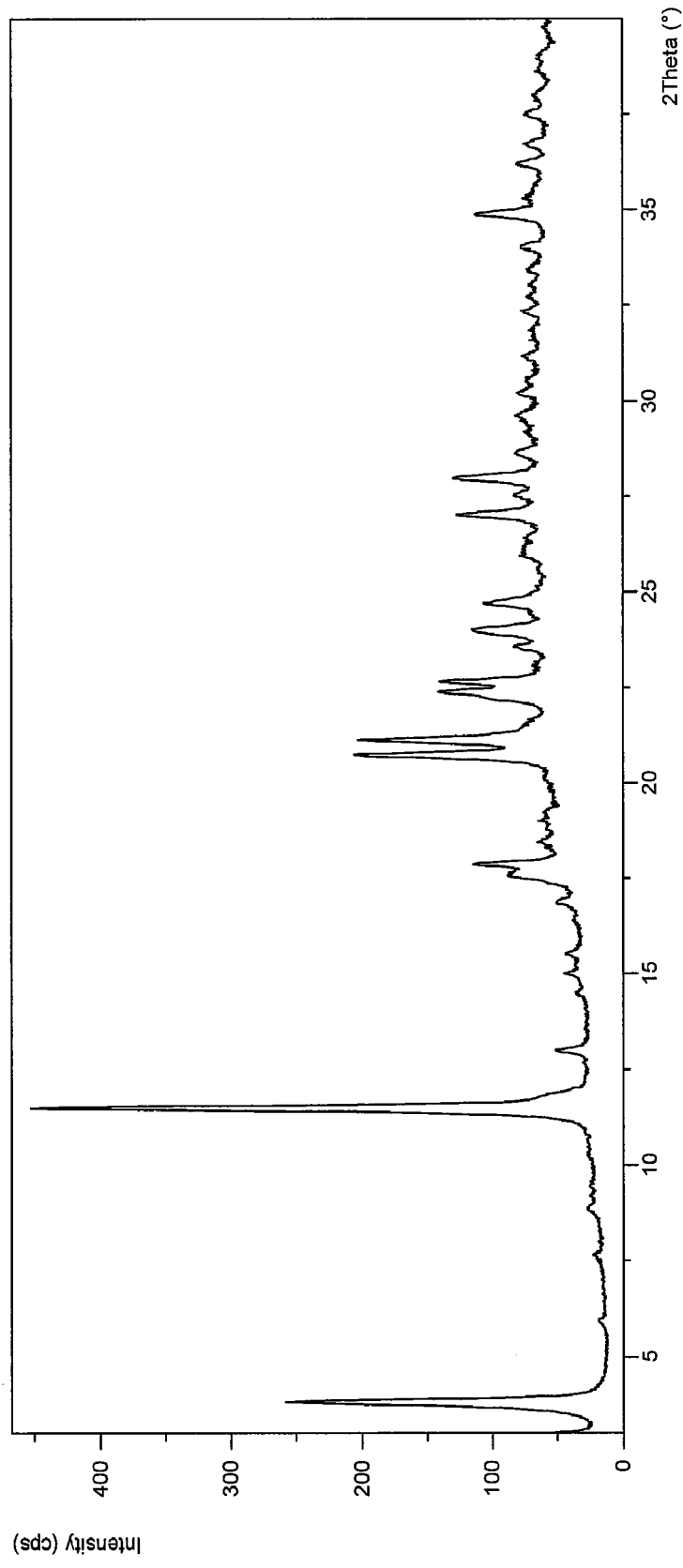
Figure 12: An X-ray powder diffractogram (XRPD) of form V of Selexipag

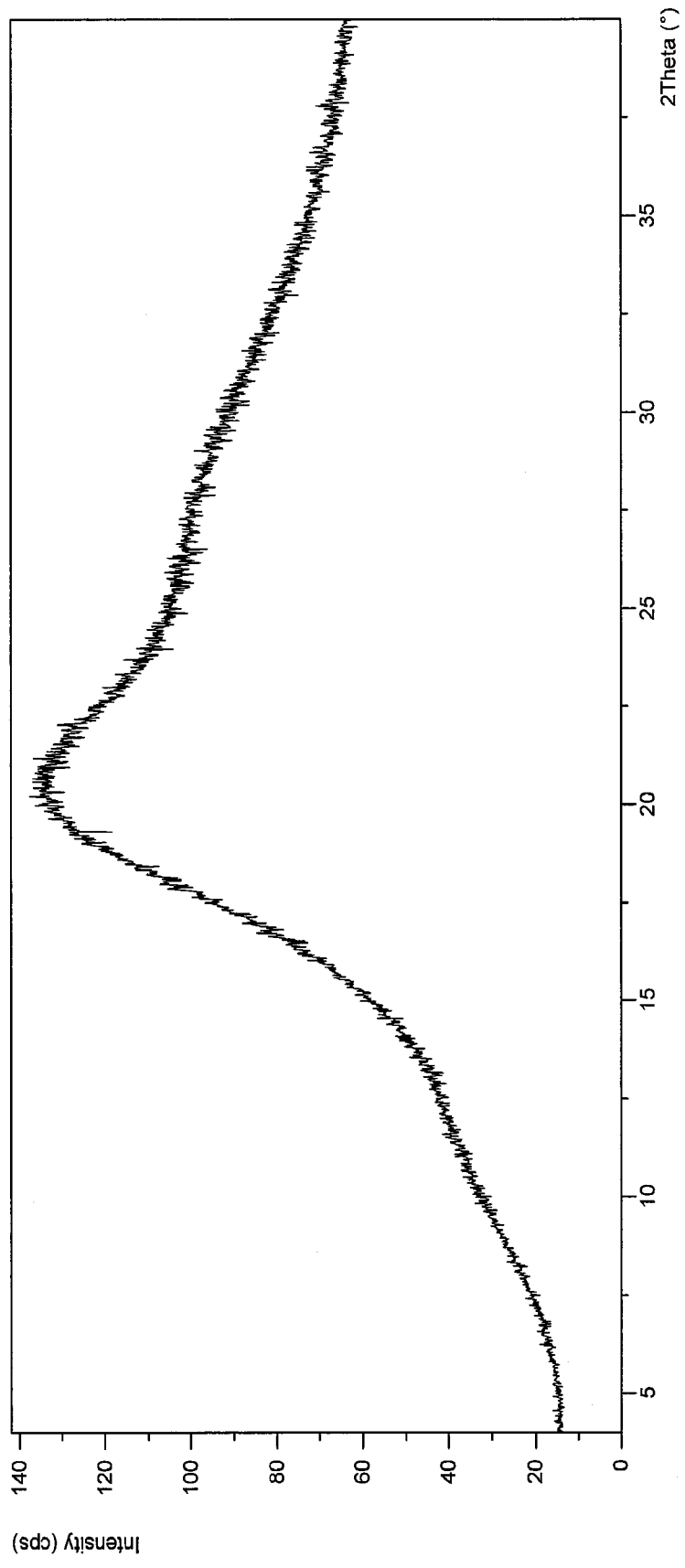
Figure 13: An X-ray powder diffractogram (XRPD) of amorphous Selexipag

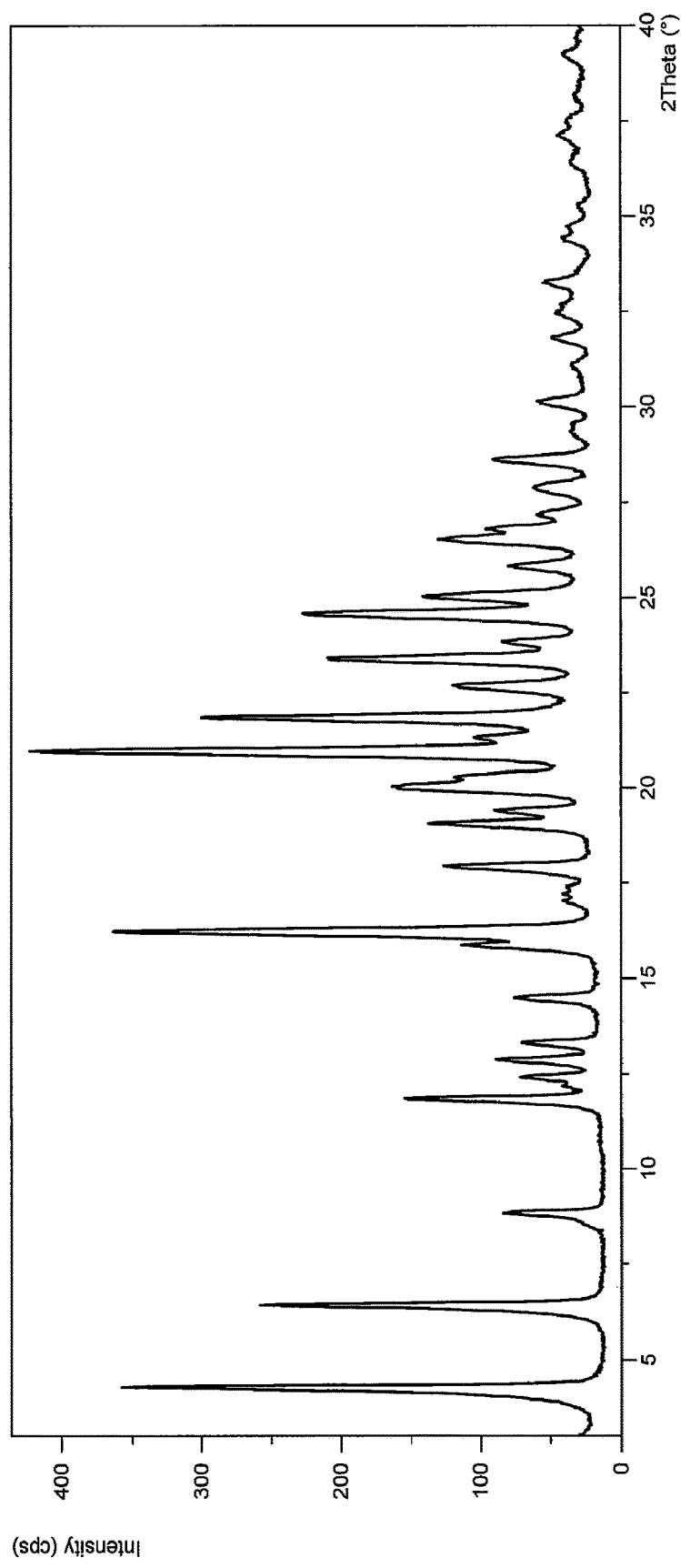
Figure 14: An XRPD of form IV of Selexipag

SOLID STATE FORMS OF SELEXIPAG

CROSS REFERENCE TO RELATED APPLICATIONS

This application is the National Stage Application of International Patent Application No. PCT/US2016/050021 filed Sep. 2, 2016 which claims the benefit of U.S. Provisional Patent Application No. 62/213,702, filed Sep. 3, 2015, U.S. Provisional Patent Application No. 62/250,955, filed Nov. 4, 2015, and U.S. Provisional Patent Application No. 62/343,617, filed May 31, 2016, the entireties of which are incorporated herein by reference.

FIELD OF THE DISCLOSURE

The present disclosure relates to solid state form of Selexipag, processes for preparation thereof and pharmaceutical compositions thereof.

BACKGROUND OF THE DISCLOSURE

Selexipag has the chemical name 2-{4-[(5,6-diphenylpyrazin-2-yl)(isopropyl)amino]butoxy}-N-(methylsulfonyl)acetamide. Selexipag has the following chemical structure:

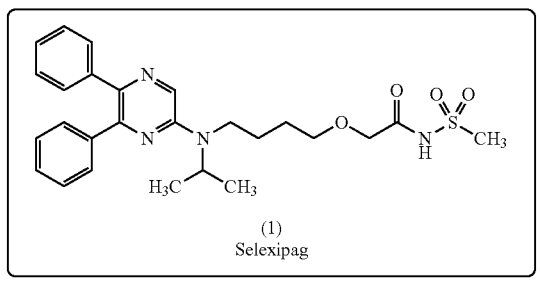 [SMILES: CC(C)N(CCCCOCC(=O)NS(C)(=O)=O)c1cnc(-c2ccccc2)c(-c2ccccc2)n1]

(1)
Selexipag

Selexipag is being developed by Actelion and Nippon Shinyaku for the treatment of arteriosclerosis obliterans, pulmonary hypertension and Raynaud's disease secondary to systemic sclerosis.

Selexipag is disclosed in U.S. Pat. No. 7,205,302. U.S. Pat. No. 8,791,122, US 2014-0148469 and US 2014-0155414 disclose polymorphs of Selexipag, denominated I, II and III.

Polymorphism, the occurrence of different crystal forms, is a property of some molecules and molecular complexes. A single compound, like Selexipag, may give rise to a variety of polymorphs having distinct crystal structures and physical properties like melting point, thermal behaviors (e.g. measured by thermogravimetric analysis—"TGA", or differential scanning calorimetry—"DSC"), X-ray powder diffraction (XRPD) pattern, infrared absorption fingerprint, Raman absorption fingerprint, and solid state ($^{13}C$—) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, improving the dissolution profile, or improving stability (polymorph as well as chemical stability) and shelf-life. These variations in the properties of different salts and solid state forms may also provide improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to use variations in the properties and characteristics of a solid active pharmaceutical ingredient for providing an improved product.

Discovering new salts, solid state forms and solvates of a pharmaceutical product can provide materials having desirable processing properties, such as ease of handling, ease of processing, storage stability, and ease of purification or as desirable intermediate crystal forms that facilitate conversion to other salts or polymorphic forms. New salts, polymorphic forms and solvates of a pharmaceutically useful compound can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life.

For at least these reasons, there is a need for additional solid state forms (including solvated forms) of Selexipag.

SUMMARY OF THE DISCLOSURE

The present disclosure relates to solid state forms of Selexipag, processes for preparation thereof, and pharmaceutical compositions comprising these solid state forms.

The present disclosure also provides uses of the solid state forms of Selexipag for preparing other solid state forms of Selexipag, Selexipag salts and solid state forms thereof.

The present disclosure also provides solid state forms of Selexipag of the present disclosure for uses in the preparation of other solid state forms of Selexipag, Selexipag salts and solid state forms thereof.

The present disclosure further provides processes for preparing other solid state forms of Selexipag, Selexipag salts and solid state forms thereof.

In another embodiment, the present disclosure encompasses the described solid state forms of Selexipag for uses in the preparation of pharmaceutical compositions and/or formulations, optionally for the treatment of arteriosclerosis obliterans, pulmonary hypertension or Raynaud's disease secondary to systemic sclerosis.

In another embodiment, the present disclosure encompasses uses of the described solid state form of Selexipag for the preparation of pharmaceutical compositions and/or formulations.

The present disclosure further provides pharmaceutical compositions comprising the solid state form of Selexipag according to the present disclosure.

In yet another embodiment, the present disclosure encompasses pharmaceutical formulations comprising the described solid state forms of Selexipag and at least one pharmaceutically acceptable excipient.

The present disclosure encompasses processes to prepare said pharmaceutical formulations of Selexipag comprising combining the described solid state form and at least one pharmaceutically acceptable excipient.

The solid state forms defined herein as well as the pharmaceutical compositions or formulations of the solid state form of Selexipag can be used as medicaments, particularly for the treatment of arteriosclerosis obliterans, pulmonary hypertension or Raynaud's disease secondary to systemic sclerosis.

The present disclosure also provides methods of treating arteriosclerosis obliterans, pulmonary hypertension or Raynaud's disease secondary to systemic sclerosis; comprising administering a therapeutically effective amount of the solid state form of Selexipag of the present disclosure, or at least one of the herein described pharmaceutical compositions or formulations, to a subject suffering from arteriosclerosis obliterans, pulmonary hypertension or Raynaud's disease secondary to systemic sclerosis, or otherwise in need of the treatment.

The present disclosure also provides uses of the solid state forms of Selexipag of the present disclosure, or at least one of the above pharmaceutical compositions or formulations for the manufacture of medicaments for treating arteriosclerosis obliterans, pulmonary hypertension or Raynaud's disease secondary to systemic sclerosis.

BRIEF DESCRIPTION OF THE FIGURES

FIG. 1 shows an X-ray powder diffractogram (XRPD) of form IV of Selexipag.
FIG. 2 shows a Le-Bail fit of Synchrotron powder diffraction pattern of Selexipag Form IV.
FIG. 3 shows a Differential scanning calorimetry thermogram (DSC) of form IV of Selexipag.
FIG. 4 shows a Thermogravimetric analysis thermogram (TGA) of form IV of Selexipag.
FIG. 5 shows a Raman spectrum (full range) of form IV of Selexipag
FIG. 6 shows a Raman spectrum (range from 1800-150 cm$^{-1}$) of form IV of Selexipag
FIG. 7 shows a FTIR (full range) of form IV of Selexipag
FIG. 8 shows a FTIR (range 1800-400 cm$^{-1}$) of form IV of Selexipag
FIG. 9 shows a $^{13}$C solid state NMR spectrum (range from 200-0 ppm) of form IV of Selexipag
FIG. 10 shows a $^{13}$C solid state NMR spectrum (range from 200-100 ppm) of form IV of Selexipag
FIG. 11 shows a $^{13}$C solid state NMR spectrum (range from 100-0 ppm) of form IV of Selexipag
FIG. 12 shows an XRPD of form V of Selexipag
FIG. 13 shows an XRPD of amorphous Selexipag.
FIG. 14 shows an XRPD of form IV of Selexipag.

DETAILED DESCRIPTION OF THE DISCLOSURE

The present disclosure relates to a solid state form of Selexipag, processes for preparation thereof and pharmaceutical compositions comprising this solid state form. The disclosure also relates to the conversion of the described solid state form of Selexipag to other solid state forms of Selexipag, Selexipag salts and their solid state forms thereof.

The solid state form of Selexipag according to the present disclosure may have advantageous properties selected from at least one of: chemical or polymorphic purity, flowability, solubility, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents and advantageous processing and handling characteristics such as compressibility, or bulk density.

A crystal form may be referred to herein as being characterized by graphical data "as depicted in" a Figure. Such data include, for example, powder X-ray diffractograms, differential scanning calorimetry (DSC), Thermogravimetric analysis (TGA) and solid state NMR spectra. As is well-known in the art, the graphical data potentially provides additional technical information to further define the respective solid state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Selexipag referred to herein as being characterized by graphical data "as depicted in" a Figure will thus be understood to include any crystal forms of the Selexipag, characterized with the graphical data having such small variations, as are well known to the skilled person, in comparison with the Figure.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% or less, about 10% or less, about 5% or less, about 2% or less, about 1% or less, or 0% of any other forms of the subject compound as measured, for example, by XRPD. Thus, the solid state form of Selexipag described herein as substantially free of any other solid state forms would be understood to contain greater than about 80% (w/w), greater than about 90% (w/w), greater than about 95% (w/w), greater than about 98% (w/w), greater than about 99% (w/w), or a 100% of the subject solid state form of Selexipag. Accordingly, in some embodiments of the disclosure, the described solid state forms of Selexipag may contain from about 1% to about 20% (w/w), from about 5% to about 20% (w/w), or from about 5% to about 10% (w/w) of one or more other solid state forms of the same Selexipag.

As used herein, unless stated otherwise, XRPD peaks reported herein are optionally measured using CuK$_\alpha$ radiation, $\lambda$=1.541874Å. Preferably, PXRD peaks reported herein are measured using CuK$_\alpha$ radiation, $\lambda$=1.541874 Å, at a temperature of 25±3° C. Alternatively, if an instrument with a different wavelength is used, for example, when using high resolution XRD method, such as synchrotron, the data may be corrected to wavelength of 1.541874 respectively.

As used herein DSC measurements are preferably obtained at a heating rate of 1° C./min; and under a nitrogen flow, preferably wherein the nitrogen flow is at the rate of 50 ml/min.

As used herein, $^{13}$C NMR spectra are preferably measured at 125 MHz at magic angle spinning (MAS) frequency $\omega_r/2\pi$=11 kHz.

As used herein, unless stated otherwise, unit cell data reported herein are optionally measured using synchrotron radiation at wavelength $\lambda$=0.399872(7) Å.

The modifier "about" should be considered as disclosing the range defined by the absolute values of the two endpoints. For example, the expression "from about 2 to about 4" also discloses the range "from 2 to 4." When used to modify a single number, the term "about" may refer to plus or minus 10% of the indicated number and includes the indicated number. For example, "about 10%" may indicate a range of 9% to 11%, and "about 1" means from 0.9-1.1.

As used herein, the term "isolated" in reference to solid state forms of Selexipag of the present disclosure corresponds to solid state form of Selexipag that is physically separated from the reaction mixture in which it is formed.

A thing, e.g., a reaction mixture, may be characterized herein as being at, or allowed to come to "room temperature", often abbreviated "RT." This means that the temperature of the thing is close to, or the same as, that of the space, e.g., the room or fume hood, in which the thing is located. Typically, room temperature is from about 20° C. to about 30° C., about 22° C. to about 27° C., or about 25° C.

A process or step may be referred to herein as being carried out "overnight." This refers to a time interval, e.g., for the process or step, that spans the time during the night, when that process or step may not be actively observed. This time interval is from about 8 to about 20 hours, about 10 to about 18 hours, or about 16 hours.

As used herein, the expression "wet crystalline form" refers to a polymorph that was not dried using any conventional techniques to remove residual solvent. Examples for such conventional techniques can be, but not limited to, evaporation, vacuum drying, oven drying, drying under nitrogen flow, etc.

As used herein, the expression "dry crystalline form" refers to a polymorph that was dried using any conventional techniques to remove residual solvent. Examples of such conventional techniques can be, but are not limited to, evaporation, vacuum drying, oven drying, drying under nitrogen flow, etc.

As used herein, and unless stated otherwise, the term "anhydrous" in relation to crystalline Selexipag relates to crystalline Selexipag which does not include any crystalline water (or other solvents) in a defined, stoichiometric amount within the crystal. Moreover, an "anhydrous" form does not contain more than about 1% (w/w) of either water or organic solvents as measured for example by TGA.

The term "solvate", as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding MTBE (1.5 v/v) to a 100 ml reaction mixture would indicate that 150 mL of MTBE was added.

As used herein the term non-hygroscopic in relation to crystalline Selexipag refers to less than about 0.2% (w/w) absorption of water at about 25° C. and about 80% relative humidity (RH) by the crystalline Selexipag as determined for example by TGA. Water can be, for example, atmospheric water.

As used herein, the term "reduced pressure" refers to a pressure of about 10 mbar to about 50 mbar.

The present disclosure comprises a crystalline form of Selexipag designated as Form IV. The crystalline Form IV of Selexipag can be characterized by data selected from one or more of the following: an XRPD pattern having peaks at 4.4, 6.6, 12.0, 16.3, and 21.1 degrees 2-theta±0.2 degrees 2-theta; an XRPD pattern as depicted in FIG. 1; and combinations of these data. Crystalline Form IV of Selexipag may be further characterized by the XRPD pattern having peaks at 4.4, 6.6, 12.0, 16.3, and 21.1 degrees 2-theta±0.2 degrees 2-theta, and also having one, two, three, four or five additional peaks selected from 12.6, 13.0, 13.5, 14.6, and 22.0 degrees two theta±0.2 degrees two theta.

Alternatively crystalline Form IV of Selexipag can be characterized by data selected from one or more of the following: an XRPD pattern having peaks at 4.3, 6.5, 11.9, 16.2, 18.0, 19.1 and 21.0 degrees 2-theta±0.2 degrees 2-theta; an XRPD pattern as depicted in FIG. 14; and combinations of these data. Crystalline Form IV of Selexipag may be further characterized by the XRPD pattern having peaks at 4.3, 6.5, 11.9, 16.2, 18.0, 19.1 and 21.0 degrees 2-theta±0.2 degrees 2-theta, and also having one, two, three, four or five additional peaks selected from: 12.4, 12.8, 13.3, 14.5, and 21.9 degrees two theta±0.2 degrees two theta.

Alternatively, crystalline Form IV of Selexipag may be characterized by the following unit cell data:

| | |
|---|---|
| Cell length a | 41.231 Å |
| Cell length b | 14.486 Å |
| Cell length c | 8.863 Å |
| Cell angle alpha | 90.00° |
| Cell angle beta | 90.00° |
| Cell angle gamma | 90.00° |
| Cell volume | 5393.47 Å$^3$ |
| Cell measurement temperature | ambient |
| Symmetry cell setting | orthorhombic |
| Symmetry space group name | Pccn |

Crystalline Form IV of Selexipag may be further characterized by a DSC thermogram substantially as depicted in FIG. 3; a DSC melting peak at about 93° C.±4° C., a DSC melting onset at about 90° C.±4° C., or combinations thereof.

The above crystalline Form IV of Selexipag may be an anhydrous form, as can be determined by TGA. In certain embodiments, the present disclosure comprises crystalline Form IV of Selexipag having up to 0.5% w/w residual solvent content; a TGA thermogram of Form IV substantially as depicted in FIG. 4; or combinations thereof.

Crystalline Form IV of Selexipag may be further characterized by Raman spectrum as depicted in FIG. 5 or 6, Raman spectrum comprising the following peak positions (±1 cm$^{-1}$):

| Peak position [cm$^{-1}$] | Raman Intensity |
|---|---|
| 192 | 27 |
| 228 | 29 |
| 253 | 25 |
| 325 | 20 |
| 353 | 20 |

-continued

| Peak position [cm⁻¹] | Raman Intensity |
|---|---|
| 407 | 28 |
| 439 | 20 |
| 513 | 17 |
| 537 | 19 |
| 586 | 13 |
| 615 | 17 |
| 666 | 12 |
| 699 | 18 |
| 718 | 20 |
| 769 | 16 |
| 802 | 17 |
| 846 | 14 |
| 884 | 13 |
| 1001 | 73 |
| 1028 | 25 |
| 1089 | 13 |
| 1156 | 21 |
| 1167 | 19 |
| 1178 | 22 |
| 1235 | 28 |
| 1318 | 45 |
| 1397 | 34 |
| 1439 | 18 |
| 1466 | 19 |
| 1499 | 59 |
| 1511 | 44 |
| 1554 | 37 |
| 1581 | 27 |
| 1599 | 119 |
| 1713 | 11 |
| 2937 | 20 |
| 3061 | 26 | and combinations thereof. The Raman spectrum may be characterized by the above peak positions (±1 cm⁻¹) alone, or optionally in combination with the corresponding Raman intensities indicated above.

Crystalline Form IV of Selexipag may be further characterized by FTIR spectrum as depicted in FIG. 7 or 8, FTIR spectrum comprising the following peaks (±1 cm⁻¹):

| Peak position [cm-1] | Transmittance [%] |
|---|---|
| 460 | 53 |
| 496 | 19 |
| 510 | 21 |
| 527 | 23 |
| 586 | 46 |
| 629 | 45 |
| 699 | 2 |
| 756 | 16 |
| 770 | 12 |
| 803 | 48 |
| 873 | 13 |
| 915 | 43 |
| 946 | 44 |
| 975 | 9 |
| 997 | 40 |
| 1008 | 19 |
| 1027 | 28 |
| 1060 | 20 |
| 1073 | 32 |
| 1111 | 2 |
| 1153 | 1 |
| 1180 | 11 |
| 1235 | 15 |
| 1265 | 49 |
| 1298 | 26 |
| 1325 | 10 |
| 1344 | 1 |
| 1365 | 10 |
| 1401 | 8 |
| 1444 | 3 |
| 1470 | 1 |
| 1514 | 9 |
| 1566 | 2 |
| 1583 | 17 |
| 1600 | 54 |
| 1722 | 2 |
| 2711 | 53 |
| 2876 | 27 |
| 2956 | 24 |
| 2980 | 25 |
| 3025 | 34 |
| 3059 | 41 | and combinations thereof. The FTIR spectrum may be characterized by the above peak positions (±1 cm⁻¹) alone, or optionally in combination with the corresponding transmittance values (%) indicated above.

Alternatively, crystalline Form IV of Selexipag may be characterized by data selected from one or more of the following: a solid state $^{13}$C NMR spectrum with peaks at 169.3, 151.0, 148.4, 147.8 and 132.4 ppm±0.2 ppm; a solid state $^{13}$C NMR spectrum having the following chemical shift absolute differences from a peak at 127.6 ppm±1 ppm of 41.7, 23.4, 20.8, 20.2, 4.8±0.1 ppm; a solid state $^{13}$C NMR spectrum as depicted in FIG. 9 or 10 or 11; and combination of these data. Crystalline Form IV of Selexipag may be further characterized by a solid state $^{13}$C NMR spectrum with peaks at 169.3, 151.0, 148.4, 147.8 and 132.4 ppm±0.2 ppm and also having one, two, three, four or five additional peaks selected from: 74.5, 70.8, 43.3, 26.9 and 26.6 ppm±0.2 ppm;

Crystalline Form IV of Selexipag may be characterized by a solid state $^{13}$C NMR having the following peak list: 228.1, 227.3, 214.9, 169.3, 151.0, 148.4, 147.8, 140.7, 139.8, 138.4, 132.4, 128.9, 127.6, 74.5, 70.8, 43.3, 41.8, 26.9, 26.6, 22.3, 21.4 and 19.0 ppm±0.2 ppm.

Crystalline Form IV of Selexipag may be characterized by each of the above characteristics alone/or by all possible combinations of, e.g. but not limited to, an XRPD pattern having peaks at 4.4, 6.6, 12.0, 16.3, and 21.1 degrees 2-theta±0.2 degrees 2-theta; an XRPD pattern as depicted in FIG. 1; by the above described unit cell data; TGA thermogram of Form IV is substantially as depicted in FIG. 4, or combinations thereof.

As discussed above, depending on which other solid state form it is compared with, Form IV of Selexipag may according to the present disclosure may have advantageous properties selected from at least one of: chemical or polymorphic purity, flowability, solubility, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents and advantageous processing and handling characteristics such as compressibility, or bulk density. Particularly, crystalline Form IV of Selexipag of the present disclosure exhibits for example enhanced solubility in aqueous medium at pH=6.7 in comparison with Form I of U.S. Pat. No. 8,791,122. The increased solubility of Form IV of Selexipag is particularly advantageous, as Selexipag Form I is practically insoluble in such a medium. The increased solubility of Form IV of Selexipag may enhance bioavailability of the API.

The present disclosure further comprises a crystalline form of Selexipag designated as Form V. The crystalline Form V of Selexipag can be characterized by data selected from one or more of the following: an XRPD pattern having peaks at 3.8, 11.5, 13.0, 17.9, 20.7, and 21.1 degrees 2-theta±0.2 degrees 2-theta; an XRPD pattern as depicted in FIG. 12; and combinations of these data. Crystalline Form V of Selexipag may be further characterized by the XRPD pattern having peaks at 3.8, 11.5, 13.0, 17.9, 20.7, and 21.1 degrees 2-theta±0.2 degrees 2-theta, and also having one, two, three, four or five additional peaks selected from 22.4, 22.7, 24.7 and 27.0 degrees 2-theta±0.2 degrees 2-theta.

The present disclosure describes amorphous Selexipag. The amorphous form can be characterized by an XRPD pattern substantially as depicted in FIG. 13.

The present disclosure also provides uses of the solid state forms of Selexipag described in any of the above embodiments, (preferably wherein the solid stage form of Selexipag is Form IV, as described in any of the above embodiments) for preparing other solid state forms of Selexipag, Selexipag salts and their solid state forms thereof.

The present disclosure also provides solid state forms of Selexipag of the present disclosure (preferably, the solid stage form of Selexipag is Form IV as described in any of the above embodiments) for uses in the preparation of other solid state forms of Selexipag, Selexipag salts and their solid state forms thereof.

The present disclosure further encompasses processes for preparing Selexipag salt or solid state forms thereof. The processes comprise preparing the solid state forms of the present disclosure (preferably Form IV as described in any of the above embodiments), and converting them to Selexipag salt. The conversion can be done, for example, by processes comprising reacting the obtained Selexipag solid state form(s) with an appropriate base to obtain the corresponding base-addition salt.

In another embodiment, the present disclosure encompasses the above described solid state forms of Selexipag (preferably Form IV as described in any of the above embodiments) for use in the preparation of pharmaceutical compositions and/or formulations, optionally for the treatment of arteriosclerosis obliterans, pulmonary hypertension or Raynaud's disease secondary to systemic sclerosis.

In another embodiment, the present disclosure encompasses uses of the above described solid state forms of Selexipag (preferably Form IV as described in any of the above embodiments) for the preparation of pharmaceutical compositions and/or formulations. The present disclosure also provides solid state forms of Selexipag of the present disclosure as described (preferably Form IV as described in any of the above embodiments) for use in the preparation of pharmaceutical compositions and/or formulations.

The present disclosure further provides pharmaceutical compositions comprising a solid state form of Selexipag according to the present disclosure. Preferably the solid state form is Form IV as described in any of the above embodiments.

In yet another embodiment, the present disclosure encompasses pharmaceutical formulations comprising the above described solid state form of Selexipag (preferably Form IV as described in any of the above embodiments) and at least one pharmaceutically acceptable excipient.

The present disclosure encompasses processes to prepare said formulations of Selexipag comprising combining the above solid state form of Selexipag (preferably Form IV as described in any of the above embodiments) and at least one pharmaceutically acceptable excipient.

The solid state forms of Selexipag as defined herein (preferably wherein the solid state form is Form IV as described in any of the above embodiments), as well as the pharmaceutical compositions or formulations thereof and at least can be used as medicaments, particularly for the treatment of arteriosclerosis obliterans, pulmonary hypertension or Raynaud's disease secondary to systemic sclerosis.

The present disclosure also provides methods of treating arteriosclerosis obliterans, pulmonary hypertension or Raynaud's disease secondary to systemic sclerosis; comprising administering a therapeutically effective amount of the solid state form of Selexipag in the present disclosure (preferably Form IV as described in any of the above embodiments), or at least one of the above pharmaceutical compositions or formulations, to a subject suffering from arteriosclerosis obliterans, pulmonary hypertension or Raynaud's disease secondary to systemic sclerosis, or otherwise in need of the treatment.

The present disclosure also provides use of the solid state forms of Selexipag the present disclosure (preferably Form IV as described in any of the above embodiments), or at least one of the above pharmaceutical compositions or formulations for the manufacture of a medicament for treating arteriosclerosis obliterans, pulmonary hypertension or Raynaud's disease secondary to systemic sclerosis.

Having described the disclosure with reference to certain preferred embodiments, other embodiments will become apparent to one skilled in the art from consideration of the specification. The disclosure is further illustrated by reference to the following examples describing in detail the preparation of the composition and methods of use of the disclosure. It will be apparent to those skilled in the art that many modifications, both to materials and methods, may be practiced without departing from the scope of the disclosure.

Analytical Methods

X-Ray Powder Diffraction Method:

Powder X-ray Diffraction was performed on PANalytical or X'Pert Pro X-Ray powder diffractometers; CuKα radiation ($\lambda$=1.541874 Å); X'Celerator detector with active length 2.1221 degrees 2-theta; laboratory temperature 25±2° C.; zero background sample holders. Prior to analysis, the samples were gently ground using a mortar and pestle to obtain a fine powder. Optionally, silicon powder can be added in a suitable amount as internal standard in order to calibrate the positions of the diffractions. The ground sample was adjusted into a cavity of the sample holder and the surface of the sample was smoothed using a cover glass.

Measurement Parameters

| | |
|---|---|
| Scan range | 3-40 degrees 2-theta |
| Scan mode | continuous |
| Step size | 0.0167 degrees |
| Step size | 42 s |
| Sample spin | 60 rpm |
| Sample holder | zero background silicon plate |

Differential Scanning Calorimetry (DSC) Method

DSC measurements were performed on a differential scanning calorimeter DSC Discovery (TA Instruments). Aluminum crucibles 40 µl were used for sample preparation. Typical sample weight was between 1 and 5 mg.

Measurement Parameters: Temperature Range at Least 25-200° C.;

| Heating rate | 1° C./min; |
|---|---|
| Nitrogen flow | 50 ml/min. |

Thermogravimetric Analysis (TGA) Method

TGA measurements were performed on a Thermogravimetric analyzer TGA851$^e$ (Mettler Toledo). Alumina crucibles 100 μl were used for sample preparation. Usual sample weight was between 5 and 15 mg.

Measurements Parameters

| Temperature range at least | 25-300° C.; |
|---|---|
| Heating rate | 10° C./min; |
| Nitrogen flow | 50 ml/min. |

X-Ray Synchrotron Measurement

The data were measured on new ID22 beamline of European Synchrotron Radiation Facility.

Measurement Parameters

| Wavelength | 0.399872(7) Å |
|---|---|
| Step size | 0.002 Å |
| Capillaries | 1.5 mm, glass No. 50 |

Raman Spectroscopy Method

Powder sample was filled into 5 mm NMR tube and Raman spectrum was recorded on Nicolet 6700 FT-IR spectrometer with NXR FT-Raman module, equipped with 1064 nmNd:YVO4 excitation laser, CaF2 beam splitter and Ge detector.

Instrument Parameters

| Spectral range: | 4000-150 cm$^{-1}$ |
|---|---|
| Resolution: | 4.0 cm$^{-1}$ |
| Number of scans: | 128 |
| Sample gain: | auto |
| Optical velocity: | 0.4747 |
| Aperture: | 29.89 |
| Laser power: | 1 W |

FTIR Spectroscopy Method

KBr pellet was prepared and FTIR spectrum was recorded on Nicolet 380 spectrometer, equipped with KBr beam splitter and DTGS KBr detector.

Instrument Parameters

| Spectral range: | 4000-400 cm$^{-1}$ |
|---|---|
| Resolution: | 4.0 cm$^{-1}$ |
| Number of scans: | 64 |
| Sample gain: | 1 |
| Optical velocity: | 0.6329 |
| Aperture: | 100 |

$^{13}$C Solid State NMR Method

The $^{13}$C CP/MAS NMR spectra were measured at 125 MHz using Bruker Avance III HD 500 WB/US NMR spectrometer (Karlsruhe, Germany, 2013) at magic angle spinning (MAS) frequency $\omega_r/2\pi=11$ kHz. Powdered sample were placed into 4 mm ZrO$_2$ rotors and standard CPMAS pulseprogram was used. During data acquisition a high-power dipolar decoupling SPINAL-64 was applied. The applied nutation frequency of B$_1$($^1$H) field was $\omega_1/2\pi=89.3$ kHz. The nutation frequency of B$_1$($^{13}$C) and B$_1$($^1$H) fields during cross-polarization was $\omega_1/2\pi=62.5$ kHz and repetition delay was 4 s. The $^{13}$C scale was calibrated with glycine as external standard (176.03 ppm—low-field carbonyl signal).

The NMR spectrometer was completely calibrated and all experimental parameters were carefully optimized prior the investigation. Magic angle was set using KBr during standard optimization procedure and homogeneity of magnetic field was optimized using adamantane sample (resulting line-width at half-height $\Delta v_{1/2}$ was less than 3.5 Hz at 250 ms of acquisition time). Taking into account frictional heating of the samples during fast rotation all NMR experiments were performed at 303 K (precise temperature calibration was performed).

EXAMPLES

Reference example: Crude Selexipag can be obtained by any method known in the art, for example by the method described in U.S. Pat. No. 7,205,302.

Example 1

Preparation of Selexipag

Step A: Preparation of 4-((5,6-diphenyl-pyrazin-2-yl)(isopropyl)amino)butan-1-ol To 50 g (0.161 mol) of 5-bromo-2,3-diphenylpyrazine, 116 g (0.884 mol, 5.5 eq/mol) of 4-(isopropylamino)-butan-1-ol and 13.33 g of KI (0.080 mol, 0.5 Eq/mol) were added. The reaction mixture was stirred, warmed and then heated up to 140° C. for about 18-20 hrs. The reaction was monitored by TLC up to completion (starting material about 1% by TLC). The reaction mixture was cooled down to room temperature. After the reaction was completed, the following work up step was performed:

Option 1: Ethyl acetate was added (500 mL, 10 vol) and the organic phase was washed with water (150 mL, 3 vol). The organic phase was separated and aqueous phase was extracted with ethyl acetate (150 mL, 3 vol). The organic phases were joined and washed with water (200 mL, 2 vol) three times.

The solvent was distilled off under vacuum at not more than ("NMT") 40° C. until 1 vol (oil appearance).

Option 2: The material (reaction mixture obtained in step a) was dissolved in acetone (250 mL, 5 vol), the solution obtained was cooled down to 0° C. to 5° C. and anti-solvent/water was added (1000 mL, 20 vol) for 40 minutes, then the suspension was stirred for about 30 minutes at about 0° C.-5° C. The solid material was filtered and washed with water (200 mL, 4 vol). Crude wet product was obtained as yellow solid yielding 101.8% Weight Yield (WY) (87% Molar Yield (MY)), HPLC purity 90.8% on area at this stage.

The crude material, obtained in either of the above described options, was purified through crystallization from acetone: heptane as follows: to a solution of 4-((5,6-diphenyl-pyrazin-2-yl)(isopropyl)amino)butan-1-ol crude in acetone (175 mL, 3.5 vol) at 0° C. -5° C., hexane (600 mL, 12 vol) dropwise in about 120 min was added, then the precipitated mixture was cooled down to about −10° C. and stirred for about 60 min. The product was filtered off and washed with hexane (250 mL, 5 vol) and dried under vacuum at 25° C. Pure product was obtained as yellowish solid yielding overall 77.2%, (66.5% MY), HPLC purity 98.2% on area.

Step B: Preparation (2-bromo-N-(methylsulfonyl)-acetamide)

To a suspension of 50 g (0.526 mol) of methanesulfonamide in toluene (625 mL, 12.5 vol) and isopropyl acetate (625 mL, 12.5 vol), 159.1 g (0.789 mol) of bromo-acetylbromide ("BAB") was added under nitrogen atmosphere. The reaction mixture was heated up to about 90° C. for about 8 hours under a nitrogen stream. The reaction was monitored by TLC up to completion (starting material about 1% by TLC). The reaction mixture was cooled down to about 40° C. and concentrated under vacuum until 10 volumes. Subsequently, toluene was added (250 mL, 5 vol) and distilling off solvents is carried out at NMT 30° C. until 10 volumes. Then was added dichloromethane (100 mL, 2 vol) and the mixture was cooled down at 0° C. and is stirred for 90 min. The solid was filtered and washed with dichloromethane (100 mL, 2 vol). Crude product was obtained as beige solid material yielding 187% WY (83% MY), HPLC purity 99.2% at this stage.

The crude material (83 g) was purified through re-slurrying with dichloromethane (166 mL, 2 vol; preferably 332 mL, 4 vol) by stirring at about 32° C. for around 60 min. The crystallization mixture was cooled down to about 0° C.-5° C. and stirred for 30 min, filtered off and washed with dichloromethane (100 mL, 2 vol). Subsequently, the material was dried at 35° C. for 24 hours. Pure and dried material was obtained as white off solid yielding overall 173%, (77% MY), HPLC purity 99.6% on area.

Step C: Preparation of (2-[4-[(5,6-diphenyl-2-pyrazinyl)(1-methylethyl)amino]butoxy]-N-(methylsulfonyl)-acetamide)—Selexipag To 10 g (0.028 mol) of 4-((5,6-diphenyl-pyrazin-2-yl)(isopropyl)amino) butan-1-ol was added a strong base (t-BuOK) (6.0 eq/mol), previously suspended in N-N-dimethylformamide solvent, within a range of from −10° C. to 40° C. under a nitrogen atmosphere and stirred for 60 min. Then, a solution of 17.9 g (3.0 eq/mol) of 2-bromo-N-(methylsulfonyl)-acetamide, previously dissolved in N-N-dimethylformamide, was added dropwise within a range of from 120 to 180 min, controlling the exothermic temperature. The reaction was monitored by TLC up to completion. Subsequently, the mixture reaction was cooled down around 5° C. and water is added by controlling the exotherm (NMT 15° C.). Finally, an acetic acid solution was added, the suspension was stirred for about 60 min at 0° C. -5° C. The product (crude) was filtered off and washed with water. An amorphous solid was obtained. The crude product was purified by crystallization from ethanol:THF.

Step D: Purification of Selexipag

Crude Selexipag can be purified by crystallization in an organic solvent for example alcohols such as ethanol, iso-amyl alcohol, iso-propyl alcohol, butanol; ethers such as tetrahydrofuran, hydrocarbons such as heptane and mixed solvents thereof.

Example 2

Preparation of (2-[4-[(5,6-diphenyl-2-pyrazinyl)(1-methylethyl)amino]butoxy]-N-(methylsulfonyl)-acetamide)—Selexipag Selexipag was prepared according to Scheme 1.

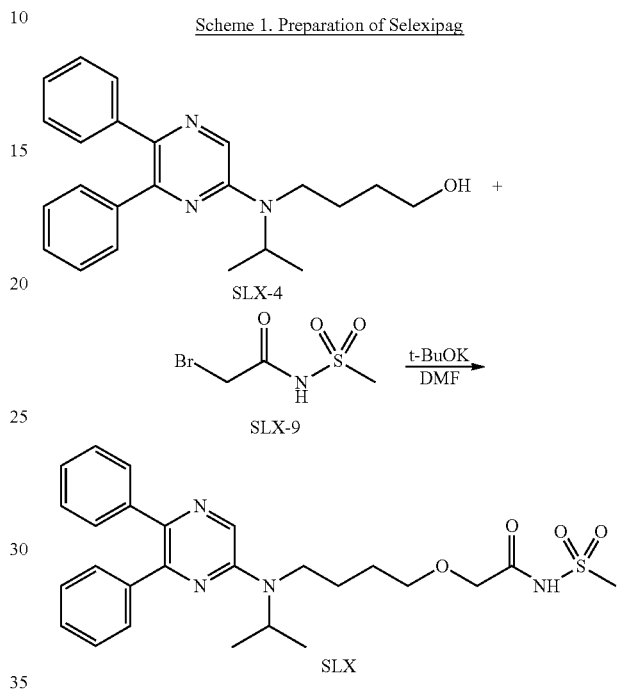

Scheme 1. Preparation of Selexipag 33.3 g (0.297 mol, 6.0 Eq/mol) of potassium tert-butoxide were dissolved in DMF (2.8 vol) in a flask (500 mL) under nitrogen atmosphere and stirred for 15 min. Then, a solution of 17.9 g (0.049 mol, 1.0 Eq/mol) of 4-((5,6-diphenyl-pyrazin-2-yl)(isopropyl) amino) butan-1-ol (SLX-4) dissolved in DMF (1.2 vol) was added in one portion. The reaction mixture was stirred for 60 min within a temperature range from 20° C. to 25° C. at 150 rpm. Then, a solution of 32.1 g (0.15 mol, 3.0 Eq/mol) of 2-bromo-N-(methylsulfonyl)-acetamide (SLX-9), previously dissolved in DMF (1.3 vol), was added dropwise for 120 minutes by controlling the temperature (exothermic process).

The reaction mixture was quenched with cool water (0.33 vol), transferred into a flask of more capacity (1000 mL) and placed in an ice bath. Cool water (38.32 vol) was added to the reaction mixture and the pH was adjusted to 5.0 with AcOH (0.33 vol). The mixture was stirred at 300 rpm for 40 min. Then, the flask with the reaction mixture was stored in the refrigerator at 8° C. After 8 h the solid was filtrated and washed with cool water (5 vol, 2 times). The crude product (yellow solid) was drained for 30 min and was stored at 8° C.

Example 3

Preparation of Crystalline Selexipag Form IV 3.0 g of Selexipag was dissolved in dimethylformamide ("DMF") (12 mL, 4 vol). The obtained solution was added dropwise to a pre-cooled acetic acid solution (0.06 M, 120 mL, from 2° C. to 8° C.), to obtain a suspension. The suspension was stirred within a range of from 2° C. to 8° C. for 30 min; then the material was filtered, washed with water (10 mL, 3.3 vol) and drained for 10 minutes. The product was analyzed by PXRD—an amorphous solid was obtained, a PXRD pattern is presented in FIG. 13. The solid material (amorphous) was suspended in heptane solvent (25 mL, 7.5 vol), the obtained suspension was stirred for 30 minutes at room temperature. The material was filtered, washed with heptane (20 mL, 6.6 vol) and drained under vacuum for at least 30 minutes at room temperature to obtain the Form-IV Crystal. The product was analyzed by PXRD—form IV was obtained. An PXRD pattern is presented in FIG. 1.

Example 4

Preparation of Crystalline Selexipag Form IV

Crude Selexipag (1.0 g, amorphous solid, obtained by the process described in Example 2) was dissolved in 5 vol), then water was added (10 vol) into the solution, the mixture was stirred for about 10 minutes and the pH was adjusted to a range of from 8.0 to 9.0 by titration with $K_2CO_3$ solution. The phases were separated; the pH of the aqueous phase was adjusted to a range of from 3.5 to 5.0 by titration with acetic acid. Then, ethyl acetate (10 vol) was added into the aqueous phase, the obtained mixture was stirred and the phases were separated. The organic phase was distilled off under reduced pressure (from 2 to 3 volumes), and a solution was obtained. The obtained solution was added to a mixture of Form IV in heptane, it was added into heptane solvent (17 vol) at a temperature of from 15° C. to 25° C., and a suspension was obtained. The suspension was filtered, washed with heptane and dried at 25° C. for about 14 hours The product was analyzed by PXRD—form IV was obtained.

The above procedure can be performed by dissolving the crude amorphous starting material in any suitable organic solvent, for example ester solvent.

Example 5

Preparation of Crystalline Selexipag Form V

A sample of crude material prepared according to example 2 was stored at 8° C. for approximately 80 hrs. The sample was analyzed by XRPD and Selexipag Form V was observed (FIG. 12)

The invention claimed is:
1. A crystalline form IV of Selexipag, characterized by data that is one or more of the following:
 (a) an XRPD pattern having peaks at 4.3, 6.5, 11.9, 16.2, 18.0, 19.1 and 21.0 degrees 2-theta±0.2 degrees 2-theta;
 (b) an XRPD pattern having peaks at 4.4, 6.6, 12.0, 16.3, and 21.1 degrees 2-theta±0.2 degrees 2-theta;
 (c) an XRPD pattern substantially as depicted in FIG. 1;
 (d) an XRPD pattern substantially as depicted in FIG. 14;
 (e) a solid state $^{13}C$ NMR spectrum with peaks at 169.3, 151.0, 148.4, 147.8 and 132.4 ppm±0.2 ppm;
 (f) a solid state $^{13}C$ NMR spectrum having chemical shift absolute differences from a peak at 127.6±1 ppm of 41.7, 23.4, 20.8, 20.2, and 4.8±0.1 ppm;
 (g) a solid state $^{13}C$ NMR spectrum as depicted in FIG. 9, 10 or 11;
 (h) a combination of one or more of (a), (d), (e), (f) and (g), or
 (i) a combination of one of more of (b), (c), (e), (f) and (g).
2. The crystalline form IV of Selexipag of claim 1, characterized by an XRPD pattern having peaks at 4.3, 6.5, 11.9, 16.2, 18.0, 19.1 and 21.0 degrees 2-theta±0.2 degrees 2-theta, and also having one, two, three, four or five additional peaks at 12.4, 12.8, 13.3, 14.5, or 21.9 degrees two theta±0.2 degrees two theta.
3. The crystalline form IV of Selexipag of claim 1, characterized by an XRPD pattern having peaks at 4.4, 6.6, 12.0, 16.3, and 21.1 degrees 2-theta±0.2 degrees 2-theta, and also having one, two, three, four or five additional peaks at 12.6, 13.0, 13.5, 14.6, or 22.0 degrees two theta±0.2 degrees two theta.
4. The crystalline form IV of Selexipag of claim 1, further characterized by data that is:
 (i) a solid state $^{13}C$ NMR spectrum with peaks at 169.3, 151.0, 148.4, 147.8 and 132.4 ppm±0.2 ppm; and also having one, two, three, four or five additional peaks at 74.5, 70.8, 43.3, 26.9, or 26.6 ppm±0.2 ppm;
 (ii) a DSC melting peak at about 93° C.±4° C.;
 (iii) a DSC thermogram as depicted in FIG. 3;
 (iv) a Raman spectrum as depicted in FIG. 5 or 6;
 (v) an FTIR spectrum as depicted in FIG. 7 or 8;
 (vi) or a combination of (i)-(v).
5. The crystalline form IV of Selexipag of claim 1, wherein the crystalline form is anhydrous.
6. The crystalline form IV of Selexipag according to claim 1, which is substantially free of any other solid state form of Selexipag.
7. A pharmaceutical composition comprising the crystalline form IV of Selexipag according to claim 1.
8. A pharmaceutical formulation comprising the crystalline form IV of Selexipag according to of claim 1 and at least one pharmaceutically acceptable excipient.
9. A process for preparing a pharmaceutical formulation, comprising combining the crystalline form IV of Selexipag of claim 1 with at least one pharmaceutically acceptable excipient.
10. A method of treating arteriosclerosis obliterans, pulmonary hypertension, or Raynaud's disease secondary to systemic sclerosis in a subject, comprising administering a therapeutically effective amount of a crystalline form IV of Selexipag of claim 1 to the subject.
11. The crystalline form IV of Selexipag according to claim 6, containing about 20% (w/w) or less, about 10% (w/w) or less, about 5% (w/w) or less, about 2% (w/w) or less, about 1% (w/w) or less, or 0% (w/w), of any other solid state forms of Selexipag.
12. A method of treating arteriosclerosis obliterans, pulmonary hypertension or Raynaud's disease secondary to systemic sclerosis in a subject, comprising administering the pharmaceutical composition of claim 7 to the subject.
13. A method of treating arteriosclerosis obliterans, pulmonary hypertension or Raynaud's disease secondary to systemic sclerosis in a subject, comprising administering the pharmaceutical composition of claim 7 to the subject.

* * * * *